US00PP25040P3

(12) United States Plant Patent
Egger

(10) Patent No.: US PP25,040 P3
(45) Date of Patent: Nov. 4, 2014

(54) **×*HEUCHERELLA* PLANT NAMED 'BUTTERED RUM'**

(50) Latin Name: ×***Heucherella* hybrid**
Varietal Denomination: Buttered Rum

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 322 days.

(21) Appl. No.: 13/507,935

(22) Filed: Aug. 7, 2012

(65) Prior Publication Data

US 2014/0047610 P1 Feb. 13, 2014

(51) Int. Cl.
*A01H 5/00* (2006.01)

(52) U.S. Cl.
USPC ..... Plt./441

(58) Field of Classification Search
CPC ..... A01H 5/02; A01H 5/00; A01H 5/12
USPC ..... Plt./441
See application file for complete search history.

(56) References Cited

PUBLICATIONS

Upov Pluto Plant Variety Database 20140812, retrieved on Aug. 14, 2014, retrieved from the Internet at <https://www3.wipo.int/pluto/user/en/index.jsp> for *Heucherella* 'Buttered Rum' QZ 20122689, 2 pp.*

Upov Pluto Plant Variety Database 20140812, retrieved on Aug. 14, 2014, retrieved from the Internet at <https://www3.wipo.int/pluto/user/en/index.jsp> for *Heucherella* 'Buttered Rum' QZ 20132664, 2 pp.*

* cited by examiner

*Primary Examiner* — June Hwu
(74) *Attorney, Agent, or Firm* — Klarquist Sparkman, LLP

(57) ABSTRACT

A new and distinct ×*Heucherella* plant substantially as shown and described, characterized by spring leaves of orange amber with a strong red pattern along veins, summer leaves amber with red brown leaf centers, fall leaves red with darker leaf centers, distinctively lobed, palmately divided leaves, small white flowers on short gray purple flower stalks, a medium plant size with multiple crowns, and excellent vigor.

3 Drawing Sheets

Botanical denomination: ×*Heucherella* hybrid.
Variety designation: 'Buttered Rum'.

BACKGROUND OF THE INVENTION

The present invention relates to a new and distinct cultivar of ×*Heucherella* and given the cultivar name of 'Buttered Rum'. *Heucherella* is in the family Saxifragaceae. ×*Heucherella* 'Buttered Rum' originated from a controlled cross between *Heuchera* K270-4 (a proprietary unreleased *Heuchera* hybrid), as the seed parent, and *Tiarella* 58-9 (a proprietary unreleased *Tiarella* hybrid), as the pollen parent.

Compared to the seed parent, *Heuchera* K270-4 (unpatented), the new cultivar has leaves that are deeply lobed and caramel to red brown colored with a red to dark blotch along the main veins compared to leaves that are shallowly lobed and tan with no blotch.

Compared to the pollen parent, *Tiarella* 58-9 (unpatented), the new cultivar has amber to red brown foliage rather than green.

Compared to ×*Heucherella* 'Brass Lantern' (U.S. Plant Pat. No. 22,396) and ×*Heucherella* 'Sweet Tea' (U.S. Plant Pat. No. 21,296), this new cultivar has a lower more compact habit, shorter flower spikes, and keeps the red tones in the foliage color all the time rather than only in the spring and fall.

This new ×*Heucherella* is distinguished by:

1. spring leaves of orange amber with a strong red pattern along veins,
2. summer leaves amber with red brown leaf centers,
3. fall leaves red with darker leaf centers.

4. distinctively lobed, palmately divided leaves,
5. small white flowers on short maroon flower stalks
6. medium plant size with multiple crowns, and
7. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a six-month-old ×*Heucherella* 'Buttered Rum' growing in a one gallon container in a cool greenhouse in early May Canby, Oreg.

FIG. 2 shows a one-year-old ×*Heucherella* 'Buttered Rum' in bloom, planted in the ground in a trial bed in the shade in late summer in Canby, Oreg.

FIG. 3 shows a one-year-old grown in a one gallon container in the greenhouse in late July.

FIG. 4 shows a 14-month-old plant in the trial bed in full sun in the winter.

DETAILED PLANT DESCRIPTION

Figure 5:
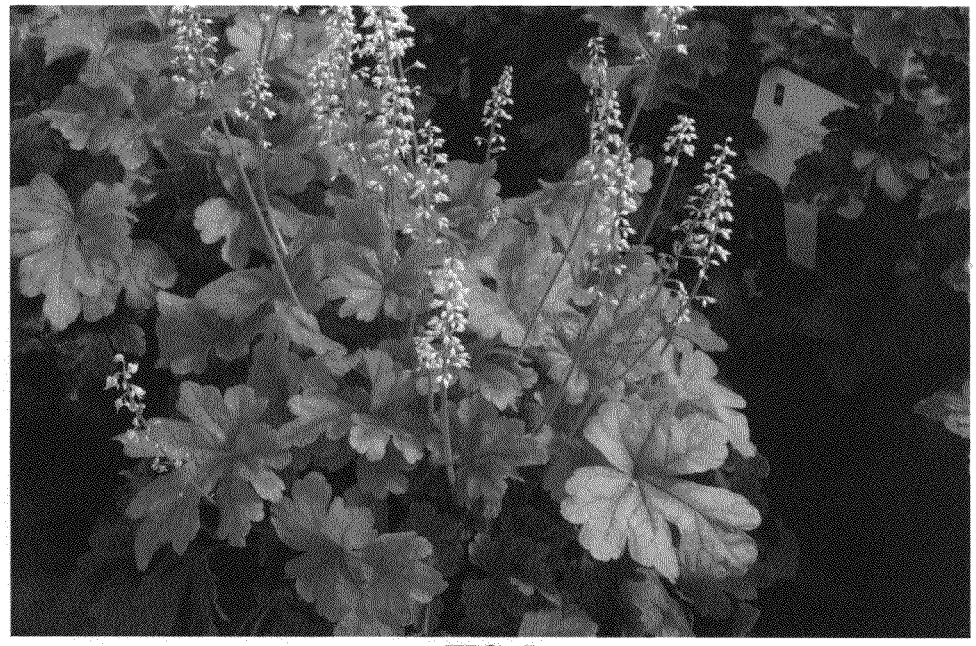
FIG. 5 shows the flowers of ×*Heucherella* 'Buttered Rum'.

The following is a detailed description of the new ×*Heucherella* cultivar based on observations of two-year-old specimens growing in one gallon containers in a cold greenhouse in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart*, fifth edition.

Plant:

*Form*.—Basal rosette, herbaceous perennial.

*Hardiness*.—USDA Zone 4 to 9.

*Size*.—19 cm tall from top of the foliage to the ground and 30 cm wide.

*Habit*.—Mounding.

*Vigor*.—Excellent.

*Roots*.—Fibrous, freely branching, fine, and white in color. Roots develop easily from cuttings.

Leaf:

*Type*.—Simple.

*Arrangement*.—Rosette.

*Shape*.—Ovate.

*Lobing/division*.—5 lobes palmately parted with the terminal the longest and most deeply parted, each with distinctly cut secondary lobes (the depth of the lobes varies with plant maturity and leaf age; leaves become more deeply lobed with maturity).

*Venation*.—Palmate.

*Margins*.—Broadly crenate, older leaves undulate or twist slightly.

*Apex*.—Mucronulate.

*Base*.—Cordate.

*Blade size*.—Grows to 10.5 cm long and 8.5 cm wide.

*Surface texture*.—Glandular both surfaces.

*Petiole description*.—Grows to 13 cm long and 2 mm wide, glandular hairs, between Purple N77C and Greyed Purple 183D.

*Leaf color*.—Spring, topside, between Greyed Orange 174A and 165B with pattern Greyed Purple 183A, bottom side closest to Greyed Red 182B; summer topside newest leaves closest to Greyed Purple 183A (lightening to Greyed Orange 165C with the pattern Greyed Red 182A), bottom side closest to Greyed Purple 183C; fall, topside, Greyed Purple 185A with venation pattern Greyed Purple N186A, bottom side N79B; winter, topside Greyed Purple 187B with venation pattern Greyed Purple N186A, bottom side N79B.

Inflorescence:

*Size*.—Grows to 2.3 cm wide and 10 cm long.

*Type*.—Raceme.

*Number of flowers per raceme*.—About 60.

*Number of raceme*.—24.

*Peduncle*.—Grows to 20 cm tall, 2 mm wide at base, Greyed Orange 166A, glandular hairs.

*Pedicel*.—Variable, with glandular hairs, Greyed Yellow 161A.

*Bloom period*.—May with sporadic rebloom in Canby, Oreg.

Flower bud:

*Size*.—2 mm wide and 3 mm long.

*Description*.—Glandular puberulent, ovoid.

*Color*.—White NN155C.

Flower:

*Type*.—Imperfect.

*Shape*.—Campanulate.

*Size*.—4 mm deep and 5 mm wide.

*Petal description*.—5 in number, lanceolate, 4 mm long and 1 mm wide, some reflexed, tip acuminate, base attenuate, margin entire, glabrous on both sides, White NN155D on both sides.

*Calyx description*.—4 mm deep and 2 mm wide, with 5 lobes, divided ¾ way to the base, campanulate, glandular hairs on outside, glabrous inside, tip obtuse, margin entire, NN155D on both sides.

*Stamen description*.—None.

*Pistil description*.—One central two beaked pistil, 4 mm long and 2 mm wide, White NN155D.

*Fragrance*.—None.

*Lastingness*.—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

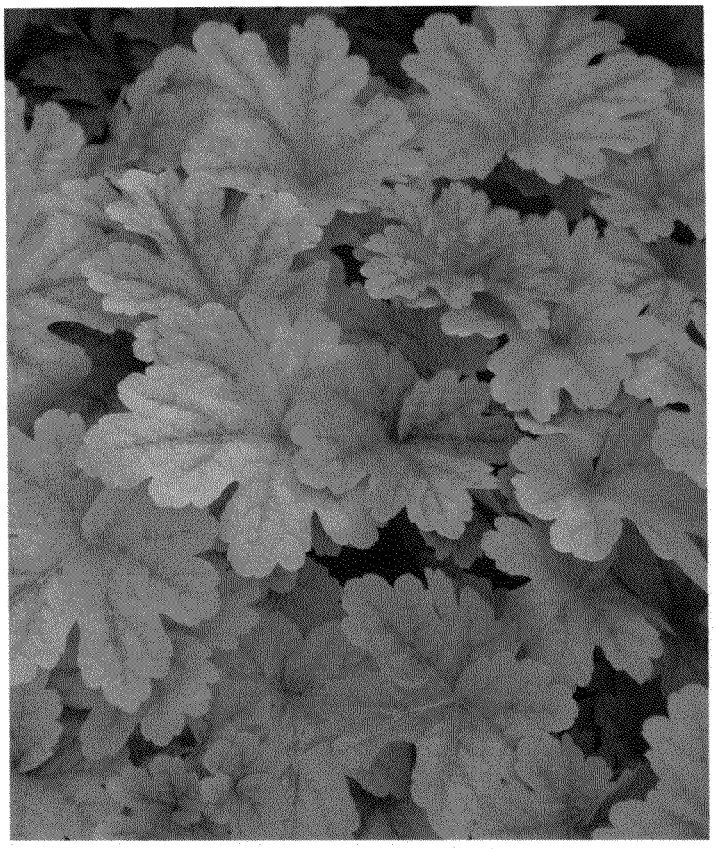
FIG. 1 above, FIG. 2 below
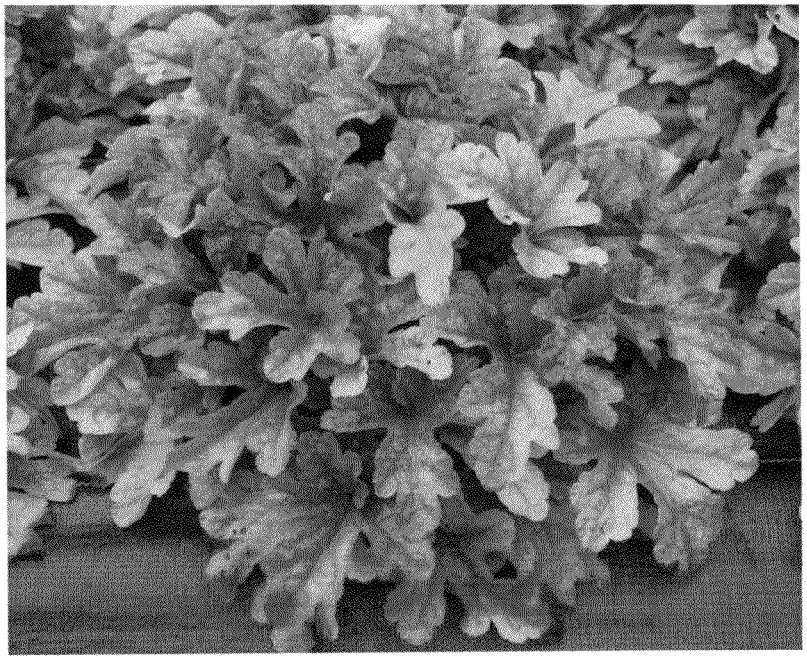

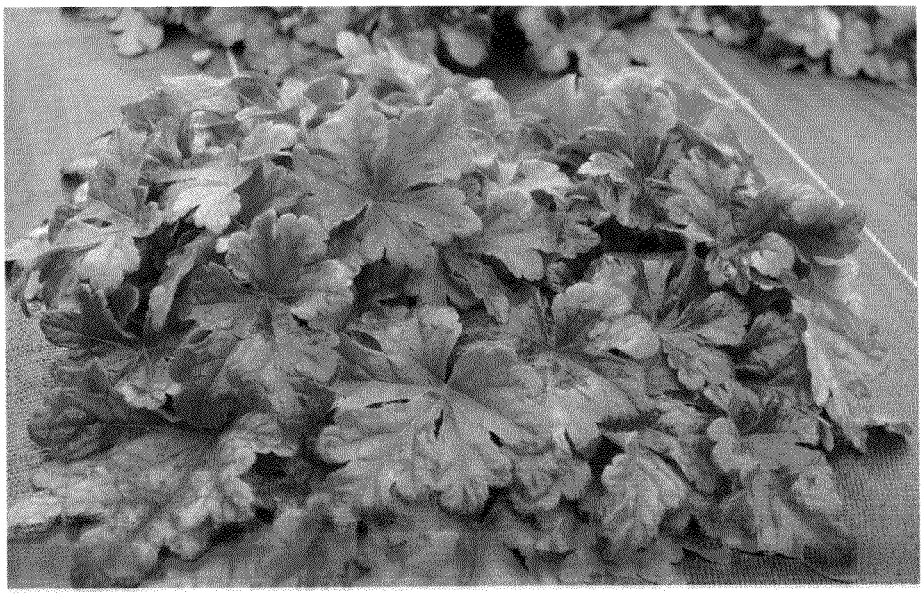

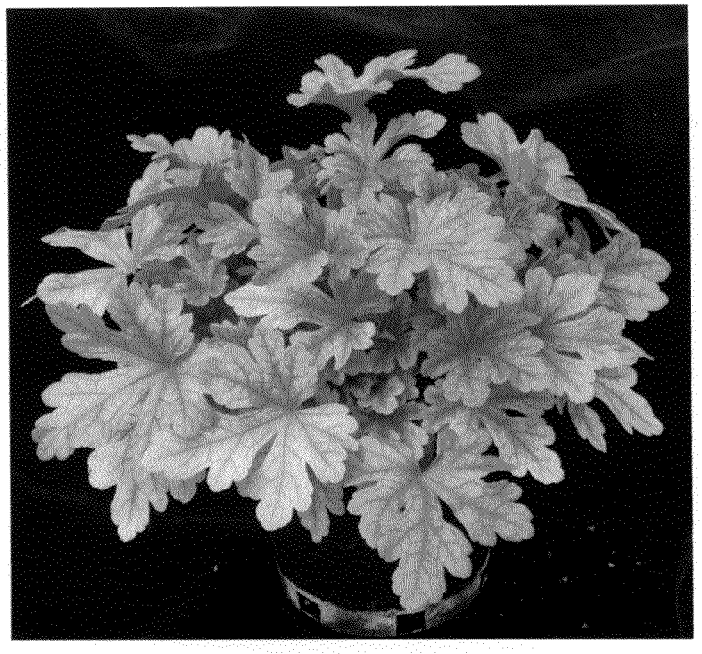
FIG. 3 above, FIG. 4 below